(12) United States Patent
Davidson

(10) Patent No.: US 6,197,043 B1
(45) Date of Patent: Mar. 6, 2001

(54) ISOELASTIC SUTURE MATERIAL AND DEVICE

(76) Inventor: James A. Davidson, 7945 Farmington Blvd., Germantown, TN (US) 38138

(*) Notice: Subject to any disclaimer, the term of this patent is extended or adjusted under 35 U.S.C. 154(b) by 0 days.

(21) Appl. No.: 09/376,227

(22) Filed: Aug. 18, 1999

(51) Int. Cl.[7] .............................. A61B 17/04; A61F 2/06; A61F 13/00

(52) U.S. Cl. ................................. 606/228; 623/1; 623/11; 623/12; 424/443

(58) Field of Search ................................... 606/228, 229, 606/230; 623/1, 11, 12; 424/443

(56) References Cited

U.S. PATENT DOCUMENTS

| | | |
|---|---|---|
| Re. 32,770 | 10/1988 | Kaplan . |
| 3,454,011 | 7/1969 | Wagner ................................. 606/228 |
| 3,954,689 | 5/1976 | Hoeschele .............................. 260/22 |
| 4,224,946 | 9/1980 | Kaplan . |
| 4,314,561 | 2/1982 | Kaplan . |
| 4,543,952 | 10/1985 | Shalaby et al. .................... 128/335.5 |
| 4,550,730 | 11/1985 | Shalaby et al. .................... 128/335.5 |
| 4,610,688 | * 9/1986 | Silvesrtini et al. ....................... 623/1 |
| 5,102,419 | * 4/1992 | Gertzman et al. .................... 606/228 |
| 5,112,900 | * 5/1992 | Buddenhagen et al. ............. 524/484 |
| 5,620,702 | 4/1997 | Podell et al. .......................... 424/448 |

OTHER PUBLICATIONS

Megerman, J. et al.; Compliance of vascular anastomoses with polybutester and polyproplyene sutures; J. Vasc. Surg. 1993; 18:827–834.

Rodeheaver, G. T. et al.; Unique Performance Characteristics of Novafil®; Surg. Gynecol. Obstet. 1987; 164:230–236.

Kim, Y. H. et al.; Flow Dynamics Across End–to–End Vascular Bypass Graft Anastomses; Annals of Biomedical Engineering; vol. 21, pp. 311–320, 1993.

Trubel, W. et al.; Compliance and Formation of Distal Anastomotic Intimal Hyperplasia in Dacrom Mesh Tube Constricted Veins Used as Arterial Bypass Grafts; ASAIO Journal; vol. 40, No. 3, pp. M273–M278, Jul.–Sep. 1994.

Trubel, W. et al.; Compliance Mismatch and Formation of Distal Anastomotic Intimal Hyperplasia in Externally Stiffened and Lumen–adapted Venous Grafts; Eur. J. Vasc. Endovasc. Surg. 10, 415–423, Nov. 1995.

Medical Data International, Inc. #RP–361287; Chapter 5: Vascular Grafts. Stents, Fabrics and Patch Materials; pp. 5-1-5-30.

M. Lei; Geometric Design Improvements for Femoral Graft–Artery Junctions Mitigating Restenosis; J. Biomechanics; vol. 29, No. 12, pp. 1605–1614, 1996.

* cited by examiner

Primary Examiner—Gary Jackson
(74) Attorney, Agent, or Firm—Fulbright & Jaworski L.L.P.

(57) ABSTRACT

A flexible, isoelastic polymer surgical suture and suture construct formed from a material selected from the group consisting of silicone, polyurethane, polyurethane copolymers, rubber, and other hemocompatible and biocompatible thermoplastic elastomers, wherein the suture and suture construct is formed from a single or multiple filament, the suture and suture construct having an elastic modulus between about 50 to 2000 psi, a tensile strength between about 500 to 50,000 psi, and a tensile elongation between about 100 to 1000 percent. In an alternate suture construct, the construct includes a base material and an inner core formed from a higher-strength fiber or group of fibers having a helical orientation. The low-modulus base material is selected from the group consisting of silicone, polyurethane, polyurethane copolymers, rubber, and other hemocompatible and biocompatible thermoplastic elastomers. In an alternate suture construct, the construct includes a base material and an inner core formed from a higher-strength fiber or group of fibers having a helical orientation. The inner core has an elastic modulus above about 2,000 psi, a tensile strength above about 10,000 psi, and a tensile elongation between about 1 to 80 percent.

19 Claims, 2 Drawing Sheets

ISOELASTIC SUTURE MATERIAL AND DEVICE

FIELD OF THE INVENTION

The present invention relates to suture materials and constructs. More specifically, the use of low-modulus, high-elongation polymeric suture materials and constructs to reduce tissue trauma and improve engagement displacement characteristics relative to adjacent blood vessel tissue.

BACKGROUND OF THE INVENTION

Blood vessels have an endothelial cell layer covering the inside surface of the blood vessel. The blood flowing through the vessel interacts with the endothelial cell (EC) layer. Blood flows at different rates through different sized vessels, and is based on an equilibrium response between the shear stress exerted on the EC layer and the vessel diameter. The vessel prefers a given shear stress, thus larger vessels reflect a lower shear stress from slower blood flow, and smaller vessels reflect the higher shear rates from faster flow. Mechanical stress also stimulates a blood vessel tissue response, with increased tissue stress (trauma) producing a thickening of the vessel wall tissue, referred to as a hyperplastic response. When vessels are repaired or replaced, the vessel ends or graft and vessel ends are attached or sewn together. This seam is called an anastomosis and it is the region of connection between blood vessels or sections of blood vessels and generally, sutures are used to create an anastomosis.

When larger diameter (above about 6 mm) blood vessels are sutured together or engaged with a woven graft to create an anastomosis, the presence of the suture creates a circumferential ring around the connected vessel anastomosis that is five to seven times stiffer than the adjacent vessel tissue (Trubel, et al, *ASAIO Journal,* 1994; *J. Vasc. Surg.,* 10, 1996). This is because available sutures utilized for vessel anastomoses are relatively stiff (high axial modulus) compared to the tissue having a low axial modulus. Although current sutures can easily bend and loop, the resistance to stretch in the long direction of the suture is very high. That is, the axial modulus is very high and more than 100 times that of the modulus of typical blood vessel tissue. Such stiff suture materials include Dacron, silk, PTFE, prolene, nylon, and polyalycolic/polylactic acid resorbable sutures.

When blood under pressure is returned to the sutured vessels, the current stiff circumferential suture ring keeps the anastomosis site from dilating in a manner similar to that of the adjacent venous or arterial vessels. When current stiff prolene and other stiff sutures are used, the stiffer anastomosis resists dilation and creates a flow discontinuity as well as a flow restriction along the inside diameter of the blood vessel. This discontinuity can be as great as one millimeter (Y. Kim and K. Chandran, *Biorheology,* 30, 117–130, 1993). While this "ridge" along the inside diameter of the vessel may be tolerable for larger diameter vessel, it creates a strong tendency for smaller-diameter vessels to thicken (hyperplasia). It also produces high and low shear regions as blood flows over the ridge.

The presence of this ridge in a coronary bypass graft anastomosis can also account for the incidences of short-term thrombosis and occlusion as well as the longer-term occlusion resulting from vessel hyperplasia and still longer-term atherosclerosis. This happens because on the downstream side of the ridge, a low shear region occurs. The low-shear stimulates the vessel to thicken which reduces its diameter and increases shear stress. This reduces the amount of allowable blood flow in the vessel. The downstream side of the ridge develops a flow eddy and low shear stress which then can form a thrombogenic process leading to occlusion (blockage) of the vessel or release of emboli (detached clots).

The presence of the discontinuity (ridge) in the vessel wall produces an increased longitudinal wall stress at the site of anastomosis (suturing), which can produce hyperplasia of the smaller diameter coronary blood vessels, a one millimeter ridge cannot be tolerated. The vessels are already less than 4 mm, and a 1 mm ridge, or even a ½-mm ridge, presents a dramatic and severe restriction to flow and a hyperplastic response from the stress concentration at the anastomosis site. It is this situation that helps to explain the poor success of woven polymer fiber vascular grafts for vessels less than about 6 mm diameter (MDI, Inc., 1996, Chap. 5), and the unsatisfactory 80 to 90 percent patency rate of coronary artery bypass grafts within one year of a bypass procedure.

Another longer term result can be the constant stress concentration from current stiff sutures within the vessel tissue which, over time, can contribute to atherosclerosis of the sutured vessel. With these results occurring with currently utilized stiff silk, prolene, nylon, and other type suture materials, it is not surprising that the anastomosed bypass vessels lose patency rapidly after surgery. One study showed these sutured vessels to have an 80 percent patency rate at one year, decreasing to as low as 20 percent at five years post-operatively (Lei, et al, *J. Biomechanics,* 29, 1996, p 1605).

U.S. Pat. No. 4,550,730 to Shalaby and Schipper describes the use of copolymers of polymethylene terephthalate that are drawn with a tensile strength greater than 60,000 psi and a modulus between 80,000 and 280,000 psi. The tensile elongation is specified between 20 and 80 percent. In contrast, the present invention describes a polymeric suture material or construct with an elastic modulus less than about 2000 psi and with a tensile elongation above about 100 percent. Additionally, the U.S. Pat. No. 4,550,730 does not describe the use or benefit of a low modulus suture of properties described in the present invention for blood vessel anastomoses.

U.S. Pat. No. 4,543,952 to Shalaby and Koelmel describes a similar suture material to that described in the U.S. Pat. No. 4,550,730, but made of polyester copolymers. Although the elastic modulus is less than 250,000 psi, the required tensile strength is above 45,000 psi. Additionally, the U.S. Pat. No. 4,543,952 does not describe or teach the use or benefit of an isoelastic suture for blood vessel anastomoses.

There are earlier patents referenced in the Shalaby patents which describe a low compliance polymer material. An example is U.S. Pat. No. 3,454,011 which proposed the use of a spandex polyurethane. However, this was proposed as a general suture material and did not specify the desirability or use of such a material for blood vessel anastomosis, as in the present invention. Similarly, U.S. Pat. No. 3,954,689 to Hoeschele et al. described a rubbery film material made of a polybutylene terephthalate thermoplastic. However, a filamentous use of this material for suturing blood vessels is not described. U.S. Pat. No. 5,620,702 also describes low-modulus films and sutures, but the construct is a laminated device with an adhesive layer and does not specify the use of a low-modulus core polymer filament with modulus less than about 2000 psi, as does the present invention. Further, the use or desirability of such a low-modulus polymer suture for improving blood vessel anastomoses is not described.

It is an object of the present invention to use polymeric suture materials that possess inherent low modulus (high stretchability, or compliance) or are constructed to have a low modulus under tension to a particular displacement. Alternatively, a higher stiffness (modulus) polymeric suture material and device can be used which is then modified in place (in-situ) via various types of energy to reduce the modulus while in place. Such thermal energy can include light, radiation, heat, vibration or a chemically activated reduction in modulus.

The inventive material or device is described as isoelastic, which means that its elastic properties closely approximate the elastic (stiffness) properties of the vessel tissue being sutured. Elastic sutures for other wound closure applications have been proposed, but with modulus of elasticity between the 500 to 2000 psi preference of the present invention. Further, a high tensile elongation (above 100 percent) as described in the present invention is not disclosed in the prior art. Specifically, there is no mention of the use of silicone, polyurethanes, its copolymers, or other thermoplastic elastomers for vessel suture applications, and which also meet the stiffness and elongation requirements of the present invention. There are also no prior art references that describe the in-situ modification of stiffer polymers via light, heat, radiation or other energy or chemically activated to reduce the modulus after suturing.

SUMMARY OF THE INVENTION

The present invention is a flexible, isoelastic polymer surgical suture and suture construct formed from a material selected from the group consisting of silicone, polyurethane, polyurethane copolymers, rubber, and other hemocompatible and biocompatible thermoplastic elastomers, wherein the suture and suture construct is formed from a single or multiple filament, the suture and suture construct having an elastic modulus between about 50 to 2000 psi, a tensile strength between about 500 to 50,000 psi, and a tensile elongation between about 100 to 1000 percent.

In an alternate suture construct, the construct includes a base material and an inner core formed from a higher-strength fiber or group of fibers having a helical orientation. The low-modulus base material is selected from the group consisting of silicone, polyurethane, polyurethane copolymers, rubber, and other hemocompatible and biocompatible thermoplastic elastomers and it has an elastic modulus between about 50 to 2000 psi, a tensile strength between about 500 to 50,000 psi, and a tensile elongation between about 100 to 1000 percent. The inner core has an elastic modulus above about 2,000 psi, a tensile strength above about 10,000 psi, and a tensile elongation between about 1 to 80 percent.

BRIEF DESCRIPTION OF THE DRAWINGS

A better understanding of the invention can be obtained when the detailed description of exemplary embodiments set forth below is reviewed in conjunction with the accompanying drawings, in which.

DETAILED DESCRIPTION OF THE PREFERRED EMBODIMENT

Figure 1:
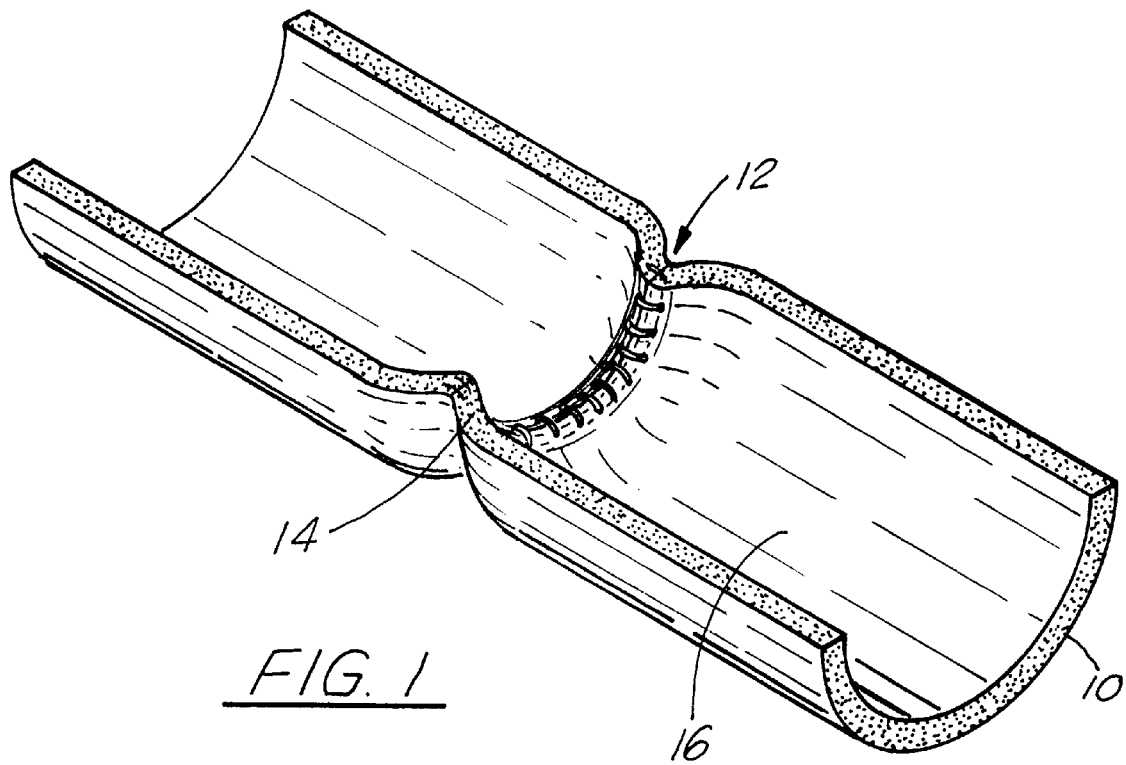
FIG. 1 is a partial, cross-sectional, schematic drawing of a blood vessel anastomosis illustrating a suture line produced by the use of a suture that is stiffer than the adjacent vessel tissue which, when dilated by pressure, produces a ridge along the blood flow path.

The present invention relates to sutures and suture constructs made from low-modulus, high-elongation polymeric materials. The use of sutures and suture constructs made from these materials will reduce tissue trauma and improve engagement displacement characteristics relative to adjacent blood vessel tissue. A low-modulus material is one that has a certain amount of elasticity and is not stiff. The polymeric material of the sutures and suture constructs can be a monofilament, or woven or braided multifilaments, or one of these in combination with a helical fiber core to increase strength under tension. The preferred polymeric materials for the inventive sutures or suture constructs are silicone, polyurethanes, its copolymers, other highly flexible and elastic rubbers, other hemocompatible and biocompatible thermoplastic elastomers, or thermoset elastic polymers. Stiffer polymers which can be modified (reduced modulus) via various energy or chemical treatments can be utilized.

The use of sutures and suture constructs made from low-modulus, high-elongation polymeric materials is desirable for the following reasons. Typical blood vessel tissues in animals, including humans, can dilate to accommodate a pressure range of between about 50 to 400 psi. The stiffness or elasticity of the vessels depends on several factors, including the patient's age and the level of vessel disease. A more typical pressure range for vessels is between about 150–300 psi. Silicone and polyurethane polymers are similarly elastic and exhibit similarly low-modulus levels, with silicone having a modulus of about 150 psi at a durometer level of 40, a modulus of about 250 psi at a durometer level of 50, and a modulus of about 400 psi at a durometer level of 60. Polyurethanes have similar moduli for the same or similar durometer levels. The tensile strength of these polymers in the 50 durometer condition is about 1000 psi, with a tensile elongation at break of well over 200 percent.

In intact human vessels, the remote axial vessel stress under 200 mm (Hg) blood pressure can be calculated to be about 7 psi. The presence of a anastomosis site increases the local axial vessel stress to about 15 psi due to the currently utilized stiff sutures. This result however, is based on the vessel tissue at the anastomosis site being healed and thus being able to accommodate this stress. An isoelastic silicone suture will accommodate this relatively low level of stress in a healed anastomosis condition. However, when an anastomosis is first sutured, there is significant stress on the suture, on the order of 150 psi. Since it takes vessel tissue a few days to heal, it thus also takes a period of time to relieve the suture of some of this stress. With a 200 mm (Hg) vessel pressure on a vessel having a 3-mm I.D. and a 4-mm O.D., and a suture diameter of 0.25 mm, and a suture spacing of 2 mm; the calculated stress on the individual silicone suture will be on the order of 150 psi. A closer suture spacing will of course reduce this suture fiber stress. For a suture spacing of 1 mm, the individual filament stress decreases to about 75 psi. Because the tensile strength of 50 durometer silicone is about 1000 psi, a silicone or polyurethane suture for small diameter vessel anastomosis will provide suitable strength while the vessel tissues heal. Thus, the need for excessive suture strength as taught in the prior art is not required for blood vessel anastomoses applications when sutures made from low-modulus, high-elongation polymeric material are used.

Figure 2:
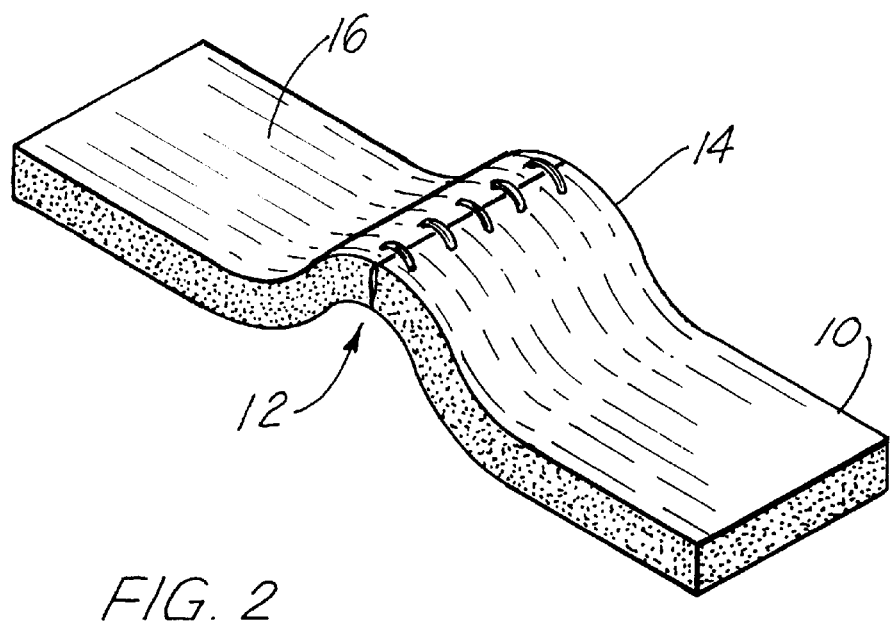
FIG. 2 is a section of the blood vessel of FIG. 1, viewed from the inside, illustrating the ridge produced by the stiff suture.
Figure 3:
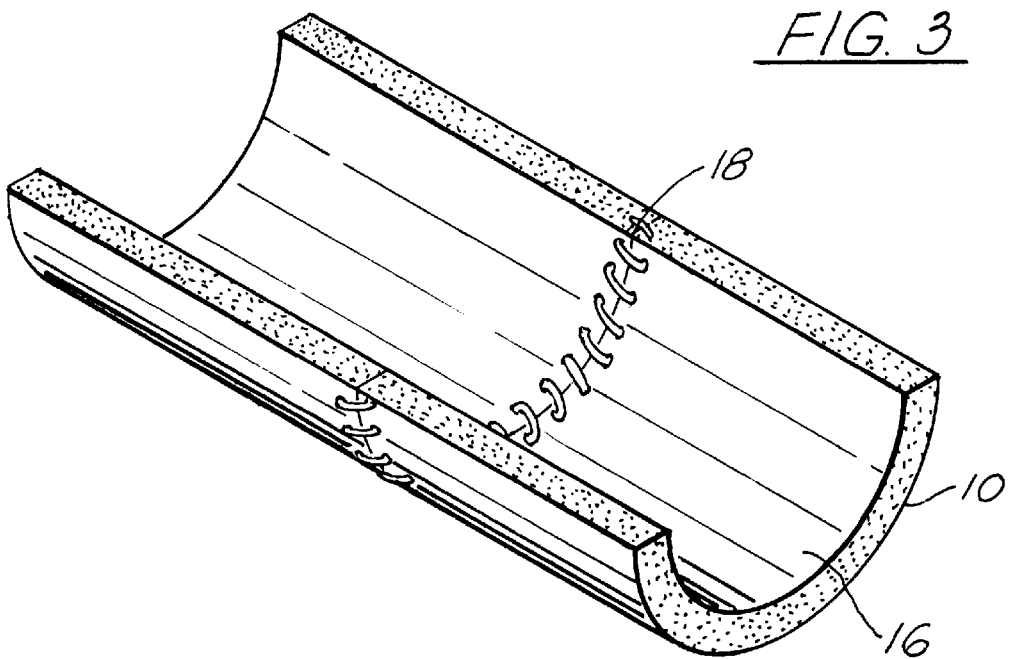
FIG. 3 is a partial, cross-sectional, schematic drawing of a blood vessel anastomosis illustrating a suture line produced by the use of the inventive low-modulus suture that expands with the vessel tissue, when dilated by pressure.

FIGS. 1 and 2 illustrate the undesirable effect of using current sutures made from polyester, silk, nylon, polypropylene, and other stiff, high-modulus material on a vessel anastomosis. When blood under pressure is returned to the sutured vessel 10, the stiffer suture region 12 will not dilate in a manner similar to that of the flexible, pressurized blood vessel 10. As a result, a ridge 14 develops along the inside diameter 16 of the vessel 10 which increases stress in the tissue and interferes with blood or other fluid flow. As illustrated in FIG. 3, the inventive suture 18, made from a monofilament or woven low-modulus, high elongation polymeric material, reduces the tendency for higher stress at the anastomosis site and eliminates the formation of the ridge 14.

Figure 4:
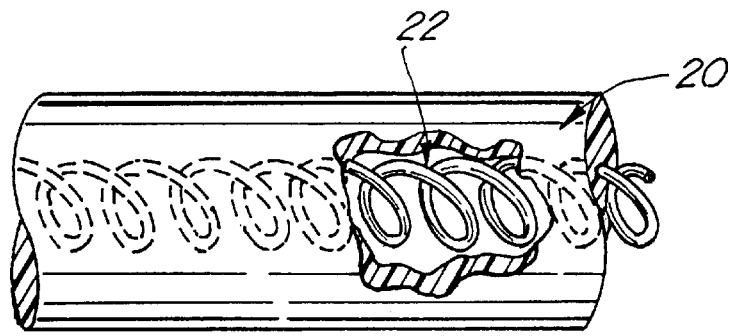
FIG. 4 is a partial, cross-sectional, schematic drawing of the inventive suture illustrating an alternative construct of the suture in a relaxed state, in which a higher-strength fiber is helically oriented and embedded into the low-modulus polymer material of the present inventive suture.
Figure 5:
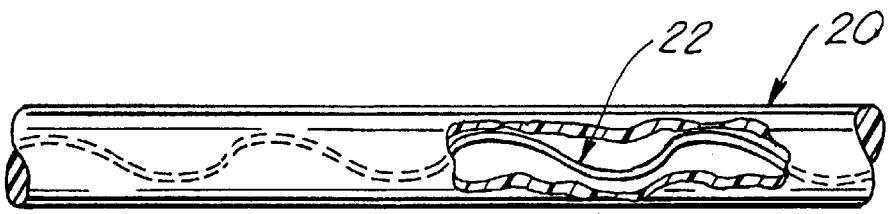
FIG. 5 is an illustration of the alternative suture of FIG. 4 in a state of tension.

An alternative suture 20 (FIG. 4) can be formed with a higher strength, higher modulus inner fiber core 22 embedded within the inventive low-modulus polymer suture 18. The inner core fiber 22 can be single or multifilament, and preferably is in a helical orientation so that the surrounding low-modulus polymer material can readily deform to reduce interference with the vessel dilation. However, as illustrated in FIG. 5, with increased tension on the suture 20, the helical core fiber 22 elongates taking up the axial load on the suture 20 after an elongation of more than 100 percent. The core fiber material and helix pitch can be varied to develop the desired resistance to elongation and elongation required to stiffen the suture. Some may prefer stiffening after about 50 percent elongation, etc. The inner core fiber or group of fibers are formed preferably of polytetrafluorethylene, silk, polyester, nylon, polypropylene, polyethylene, or metal.

The polymer material of the inventive suture and suture construct has an elastic modulus of less than about 2000 psi, at a tensile elongation of less than about 200 percent. Preferably, this elastic modulus is between about 50 to 500 psi. The tensile strength of the inventive suture and suture construct formed from isoelastic material is between about 500 to 50,000 psi without the use of the helical central fiber core 22. The tensile elongation is between about 100 to 1000 percent. With the core 22, the elastic modulus is above about 2,000 psi, and the tensile strength is above about 10,000 psi and can extend upward to 300,000 psi or greater if desired. The tensile elongation is between about 1 to 80 percent.

The inventive suture has a diameter of between about 0.1 and 1 mm. It can also be treated with anti-thrombotic agents such as heparin, hyaluronan, phosphorylcholine, platelet factors, peptides, and other proteins. Such agents can be impregnated or processed into the polymer suture material as well as being coated on or added to the suture surface to improve hemocompatibility.

The suture and suture construct can also include a surgical needle attached to at least a first end of the suture for sewing the vessel walls together. In the suture construct that includes an inner core, the needle can also engage at least a first end of the inner core.

The use of sutures and suture constructs formed from the isoelastic material will dramatically reduce local tissue stress at a vessel anastomosis site and will also reduce or eliminate the formation of a ridge along the inside diameter of the vessel at the anastomosis. This has been demonstrated with a low-modulus rubber tube, similar in size and elasticity to a human vessel under pressure. In the first test, the rubber tube was restricted along the outside diameter with a small ring of the same isoelastic material that was used for the low-modulus tube. The tube was placed under pressure and the isoelastic ring or restrictor produced only a small, 1-mm high ridge along the inside diameter, that did not increase with increasing pressure. In the second test, a silk suture was used to restrict the rubber tube. The tube was placed under the same amount of pressure and a 3-mm ridge resulted, that increased with increasing pressure. Because the isoelastic suture will be utilized in a continuous helical seam along the periphery of the anastomosis (versus a continuous ring), it is expected that a much smaller ridge, if any, will result.

The inventive suture and suture constructs formed from isoelastic materials are preferred for blood vessel anastomoses as well as suturing of other body conduits, vesicles, and tissues which may not necessarily be blood-containing conduits. Further, the inventive suture and suture constructs formed from isoelastic material are useful for attachment of blood and other vessels and conduits to grafts, stents, patches and shunts or percutaneous devices to reduce tissue trauma and subsequent tissue growth, hyperplasia, downgrowth, and similar trauma-induced response by the sutured tissue, including the suturing of heart valves.

One skilled in the art will readily appreciate that the present invention is well adapted to carry out the objects and obtain the ends and advantages mentioned, as well as those inherent therein. The inventive sutures and suture constructs described herein are presently representative of the preferred embodiments, are exemplary, and are not intended as limitations on the scope of the invention. Changes therein and other uses will occur to those skilled in the art which are encompassed within the spirit of the invention and are defined by the scope of the claims.

What is claimed is:

1. A flexible, isoelastic polymer surgical suture and suture construct formed from a material selected from the group consisting of silicone, polyurethane, polyurethane copolymers, rubber, and hemocompatible and biocompatible thermoplastic elastomers, wherein the suture and suture construct is formed from at least a single filament, the suture and suture construct having an elastic modulus between about 50 to 2000 psi, a tensile strength between about 500 to 50,000 psi, and a tensile elongation between about 100 to 1000 percent.

2. The suture and suture construct of claim 1, wherein the filament is woven.

3. The suture and suture construct of claim 1, wherein the material is in a monofilament form and is selected from the group consisting of silicone, polyurethane and polyurethane copolymers, the suture and suture construct for use in suturing blood vessels.

4. The suture and suture construct of claim 1, wherein anti-thrombotic agents are incorporated into the polymeric material.

5. The suture and suture construct of claim 4, wherein anti-thrombotic agents are selected from the group consisting of heparin, hyaluronan, phosphorylcholine, platelet factors, peptides, and other proteins.

6. The suture and suture construct of claim 1, wherein anti-thrombotic agents coat the material forming the suture and suture construct.

7. The suture and suture construct of claim 6, wherein anti-thrombotic agents are selected from the group consisting of heparin, hyaluronan, phosphorylcholine, platelet factors, peptides, and other proteins.

8. The suture and suture construct of claim 1, wherein the filament is braided.

9. The suture and suture construct of claim 1, wherein the suture and suture construct is formed from multiple filaments.

10. The suture and suture construct of claim 9, wherein the multiple filaments are woven.

11. The suture and suture construct of claim 9, wherein the multiple filaments are braided.

12. A flexible, isoelastic polymer surgical suture construct consisting of:
   a) a low-modulus base material selected from the group consisting of silicone, polyurethane, polyurethane copolymers, rubber, and hemocompatible and biocompatible thermoplastic elastomers;
   b) an inner core formed from a single higher-strength fiber;
   c) the base material having an elastic modulus between about 50 to 2000 psi, a tensile strength between about 500 to 50,000 psi, and a tensile elongation between about 100 to 1000 percent; and
   d) the inner core having an elastic modulus above about 2,000 psi, a tensile strength above about 10,000 psi, and a tensile elongation between about 1 to 80 percent.

13. The suture construct of claim 12, wherein the inner core fiber is selected from the group consisting of polytetrafluorethylene, silk, polyester, nylon, polypropylene, polyethylene, and metal.

14. The suture construct of claim 12, wherein the inner core fibers woven.

15. The suture construct of claim 12, wherein the base material is impregnated with an anti-thrombotic agent.

16. The suture construct of claim 12, wherein the base material is coated with an anti-thrombotic agent.

17. The suture construct of claim 12, wherein the base material is impregnated and coated with an anti-thrombotic agent.

18. The suture construct of claim 12, wherein the inner core is formed from a group of fibers having a helical orientation.

19. The suture construct of claim 12, wherein the inner core fibers are braided.

* * * * *